US010408767B1

United States Patent
Pearcey

(10) Patent No.: US 10,408,767 B1
(45) Date of Patent: Sep. 10, 2019

(54) SYSTEM AND METHOD FOR DETECTING IMPERFECTIONS IN A REFLECTIVE SURFACE

(71) Applicant: HATCH LTD., Mississauga (CA)

(72) Inventor: Owen Pearcey, Oakville (CA)

(73) Assignee: HATCH LTD., Mississauga (CA)

( * ) Notice: Subject to any disclaimer, the term of this patent is extended or adjusted under 35 U.S.C. 154(b) by 0 days.

(21) Appl. No.: 16/007,411

(22) Filed: Jun. 13, 2018

(51) Int. Cl.
  *G01B 11/14* (2006.01)
  *G01N 21/88* (2006.01)
  *G01N 21/95* (2006.01)

(52) U.S. Cl.
  CPC ......... *G01N 21/8806* (2013.01); *G01B 11/14* (2013.01); *G01N 21/95* (2013.01); *G01N 2201/06113* (2013.01)

(58) Field of Classification Search
  CPC ..... G01N 21/8806; G01N 21/95; G01B 11/14
  USPC ...................................................... 356/237.2
  See application file for complete search history.

(56) References Cited

U.S. PATENT DOCUMENTS

| 5,903,342 A * | 5/1999 | Yatsugake | G01N 21/94 250/559.41 |
| 2005/0219518 A1* | 10/2005 | Korngut | G01N 21/47 356/237.2 |
| 2011/0170090 A1* | 7/2011 | Naftali | G01N 21/47 356/237.2 |

\* cited by examiner

*Primary Examiner* — Roy M Punnoose
(74) *Attorney, Agent, or Firm* — Borden Ladner Gervais LLP; Brandon L. Evenson

(57) ABSTRACT

A system and method for identifying imperfections in a reflective surface. The reflective surface may be a metal coating on a sheet such as in a galvanization process. The system comprises a laser detector. The laser detector may be part of a triangulation unit. The laser detector takes readings corresponding to the angles of travel of diffuse light of a laser off of different portions of the reflective surface. Imperfections in the surface are identified based on variance in the readings. The method comprises detecting diffuse light of a laser beam off of different portions of the reflective surface, and identifying imperfections based on variances in the angles of travel of the diffuse light detected.

23 Claims, 7 Drawing Sheets

SYSTEM AND METHOD FOR DETECTING
IMPERFECTIONS IN A REFLECTIVE
SURFACE

FIELD

The present disclosure relates to the field of reflective surface quality control and metal coating processes, including galvanization processes.

BACKGROUND

Sheets of metal (which can include strips of metal) are coated with a material to provide the metal with certain desired physical properties. For example, sheets of steel are coated with a protective zinc-based material in a process known as galvanization. The protective coating inhibits the sheet from oxidizing. Galvanized sheet metal is used for automotive applications, such as car door panels.

In a conventional galvanization process line, a long sheet/strip of metal is drawn off a reel and continuously fed, using a series of rollers and guides, through a bath of molten zinc-based material. Molten zinc-based coating is typically reflective. Upon emerging from the bath the coated portion of the sheet passes between air knives. The air knives expel high pressure/velocity air onto both sides of the sheet to force excess molten coating off the sheet and preferably back into the bath.

It is important to precisely control the amount or thickness of zinc-based coating on the metal sheet. It is also important to limit the defects/imperfections in that coating. The coating can be very expensive. Too much coating increases material costs with potentially no functional benefits or way to recoup such costs in the market. Too little coating, or imperfections/defects in the coating, may result in the sheet not meeting certain industry specifications, and may prevent selling the sheet at a premium price. This is because too little coating and/or imperfections/defects in the coating could cause the sheet to be more susceptible to oxidation, or affect the appearance of a subsequently painted panel or product using the sheet, thereby limiting the applications for which it can be used and the lifetime of the sheet.

The proximity of the air knives to the sheet is one of the main parameters used to control the coating thickness. The metal sheet can, however, buckle, warp, bow, and tremble around the area of the air knives as the sheet continuously passes between the air knives. This can cause rapid changes in the distance between each air knife and the sheet, resulting in variations in coating thickness, and potentially imperfections in the coating surface. Typically, the closer the air knives are to the sheet, the better control there is over coating thickness. But the closer the air knives are to the sheet, the greater the risk that sheet movement/deformation will result in the sheet hitting an air knife. This can block the air knife vents with coating material, potentially damage the air knife, introduce imperfections into the coating, and potentially require the shutdown of the entire galvanization line.

Methods have been proposed to reduce unintended variations in the distance between the air knifes and the sheet by detecting a change in the desired distance and rapidly compensating for that change. In a method, an ultrasonic sensor is used to sense the distance between the air knife and sheet, and the air knife and sheet are moved relative to each other to compensate for variations in the desired distance. However, ultrasonic sensors can fail to accurately report a distance to a hot surface. In another method, an induction sensor is used to sense the distances between the air knifes and the sheet, and corrections are made to compensate for detected distance variations. However, induction sensors have a limited sensing range and do not cover the full scope of operating conditions. An inductive sensor with a sufficient range would be excessively large and highly nonlinear.

A reliable method of detecting the distance to a reflective surface is desirable. More specifically, a reliable method of detecting the distance from an air knife to a reflective zinc coated surface in a continuous coating process is desirable.

Imperfections can also occur in the coating of a surface. In a sheet metal galvanization process, imperfections may affect a section or area of the coating on the metal sheet. The actual size of each imperfection may be quite small (such as less than 0.1 millimeters), but the overall affected section or area may be quite large. The cause of imperfections may vary. Camera-based surface inspection systems are sometimes used to detect certain types of defects by taking a picture of the sheet and trying to identify defects based on the aggregate picture data through image recognition algorithms, for example. Such systems are typically located, however, much further down the line from the metal bath coating stage where the problem originates. This can result in a considerable amount of product being processed by the line before a problem is detected.

A method for identifying the existence of imperfections, and the extent or severity of the imperfections, is desirable. A method for early detection of imperfections in the coating process is also desirable so the cause can be more easily identified and more quickly remediated.

DETAILED DESCRIPTION

Figure 1:
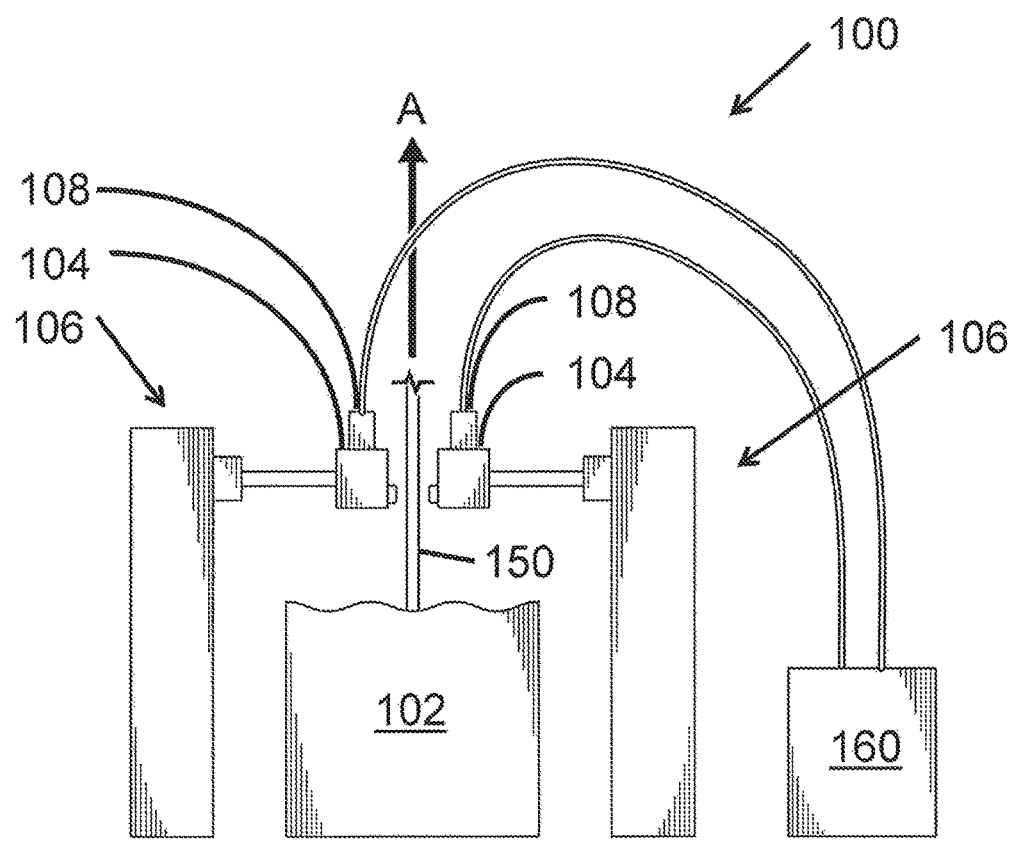
FIG. 1 shows a front view of a portion of a continuous sheet metal coating system in accordance with an embodiment of the present disclosure.

In an embodiment of the present disclosure, variances in distance readings of a laser detector are used to identify imperfections in a reflective surface. The readings may also be used to simultaneously determine a distance to the reflective surface. The laser detector may be part of a laser triangulation unit. The laser triangulation unit may employ a traditional laser light source, or a light source which produces a light beam with properties that are similar to a traditional laser beam, such as a focused light emitting diode (LED) light source.

In the embodiment, the laser triangulation unit is configured to emit a laser beam. The laser beam may be emitted at the reflective surface, at an angle to the perpendicular of the surface, to cause the beam to reflect off of the reflective surface and project onto a diffuse surface. Alternatively, the laser beam may be projected directly onto a diffuse surface. In either case, the laser beam produces a visible dot at the point it hits the diffuse surface. This is also referred to herein as a laser dot. The dot may be visible only to a particular type of detector. The laser triangulation unit detects the reflection of the laser dot on the diffuse surface. In other words, the laser triangulation unit detects, off of the reflective surface, the diffuse light of the laser dot. The triangulation unit uses the angle of travel of this received diffuse light in triangulation calculations to provide a distance reading. While the laser triangulation unit scans a particular point to produce distance readings, the reflective surface is moved in the direction of its plane through the point being scanned. A variance in the distance readings is used to identify an imperfection in the reflective surface. The variance corresponds to the imperfection passing through the diffuse light of the laser beam. The variance may appear as a disturbance or spike in the distance readings. The variance or disturbance/spike may be caused by the imperfection in the reflective surface changing the angle of travel of a portion of the diffuse light of the laser dot when the diffuse light reflects back towards the laser detector (also referred to as sensor). The change in the angle of travel of the diffuse light which occurs when the diffuse light reflects off a portion of the reflective surface with an imperfection, may be different that the change in angle of travel which occurs when the diffuse light reflects off a portion of the reflective surface without an imperfection.

Laser triangulation units determine the distance to a target diffuse surface based on the angle of travel of diffuse light returning to the laser detector from that target diffuse surface. And the distance readings of the laser triangulation unit are typically based on the angle of travel of the portion of diffuse light corresponding to the greatest distance. The portions of the diffuse light corresponding to smaller distances are filtered out by the laser triangulation unit. Accordingly, the change in the angle of travel of at least some of the diffuse light from the imperfection, as that portion of the surface with the imperfection moves past the point being scanned by the laser triangulation unit, may appear as a spike or a similar type of disturbance in the distance readings in accordance with an embodiment of the present disclosure. If the laser beam is directed at the reflective surface, the actual distance between the laser triangulation unit and the reflective surface may also be determined based on the distance reading of the triangulation unit.

In an embodiment, a system for detecting imperfections in a reflective surface comprises a laser triangulation unit configured to emit a laser beam and detect, from the reflective surface, diffuse light of the laser beam; and a computer configured to receive readings from the laser triangulation unit, the readings corresponding to angles of travel of the diffuse light, and identify imperfections in the reflective surface based on variances between the readings for different portions of the reflective surface. The system may be for use in a metal sheet galvanization process, wherein the reflective surface is a molten coating on the metal sheet. The computer may be configured to identify an imperfection in the reflective surface based on a first reading being greater than a second reading by a threshold amount. The computer may be configured to identify an imperfection in the reflective surface based on a disturbance in the readings. The computer may be configured to determine the number of the disturbances within a period of time. The triangulation unit may be configured to provide a reading corresponding to the portion of the diffuse light having the longest distance of travel. The laser triangulation unit may be configured to project the laser beam off of the reflective surface onto a diffuse surface to produce the diffuse light. The laser triangulation unit may be configured to emit the laser beam at the reflective surface at an angle to the perpendicular of the reflective surface. The laser triangulation unit may comprise a housing with a diffuse surface, and the laser triangulation unit may be configured to project the laser beam on the housing to produce the diffuse light. The system may comprise an air knife for directing air on the molten zinc coating on the sheet, and the computer may be further configured to determine the distance between the air knife and the reflective surfaces based on the readings.

In another embodiment, a system for identifying imperfections in a zinc-based coating on a metal sheet in a galvanization process may comprise a laser emitter configured to emit a laser beam at the reflective zinc-based coated surface of the metal sheet, at an angle to the perpendicular of the surface, to project a laser dot on a diffuse surface; a detector configured to detect, from the reflective zinc-coated surface, the angles of travel of diffuse light of the laser dot; and a processor configured to receive readings from the detector, the readings corresponding to the angles of travel of the diffuse light; and identify imperfections in the reflective coating based on variances in the readings for different portions of the reflective surface.

A method for detecting imperfections in a reflective surface, may comprise emitting a laser beam; detecting, off the reflective surface, diffuse light of the laser beam; determining values corresponding to the angles of travel of the diffuse light received off of different portions of the reflective surface; and identifying the imperfections in the reflective surface based on variances in the values. The method may be for use in a metal sheet galvanization process, wherein the reflective surface is a molten zinc coating on the metal sheet. Determining the values may comprise determining the distances travelled by the laser beam as collimated light. The distances may be determined based on triangulation. The imperfections in the reflective surface may be identified based on a difference between a first value and a second value, the difference being greater than a threshold amount. The first and second values may be from two consecutive laser beam scans. The imperfections in the reflective surface may be identified based on disturbances in the values. The method may further comprise determining the number of disturbances in a period of time. The laser beam may be projected off the reflective surface onto a diffuse surface to produce the diffuse light. The laser beam may be emitted at the reflective surface at an angle to the perpendicular of the reflective surface. The reflective surface may be moved in the direction of its plane relative to the path of the diffuse light.

FIG. 1 shows a front view of a portion of a continuous sheet metal coating system 100 in accordance with an embodiment of the present disclosure. The system 100 comprises molten zinc-based coating bath 102 through which a metal sheet 150 is continuously drawn in the direction of arrow A, which is in the direction of the plane of the metal sheet 150. The system 100 also comprises a pair of opposing air knives 104 on either side of the metal sheet 150 above the bath 102. An air knife is effectively a manifold with a slit opening through which air is expelled at a high pressure/velocity. The air knives 104 are mounted on a frame 106. Actuators may be used to adjust the distance of the air knives 104 relative to the sheet 150.

As the metal sheet 150 emerges from the bath 102, the air knives 104 direct air onto the zinc-based coating on both sides of the sheet 150. The force of the air helps remove excess liquid coating from the surface of the sheet, potentially by blowing the liquid coating back into the bath 102. This inhibits wasting expensive coating material, more evenly distributes the coating on the sheet 150, and helps cool the coating on the sheet 150.

In accordance with an embodiment of the present disclosure, the system 100 also comprises one or more laser triangulation units 108 in communication with a computer 160. The computer 160 may be a programmable logic controller, a microcontroller, or any other similar device which can perform general computing functions. The laser triangulation unit 108 may be any device or system comprising a laser emitter to emit a laser beam and a laser detector, and which provides a reading corresponding to the angle of return (angle of travel), relative to the laser detector, of diffuse light of the laser beam from a target diffuse surface. One or more laser triangulation units 108 may be mounted on one or both air knives 104 as shown in FIG. 1. Alternatively, the laser triangulation unit(s) 108 may be mounted on another point which is positioned relative to the air knives 104. The computer 160 may be attached to the laser triangulation unit 108.

As further described below in relation to FIGS. 2A and 2B, the triangulation unit(s) 108 is configured to detect the reflection, in the reflective zinc-based coated surface, of a laser dot being projected on a diffuse surface. The laser dot is actually diffuse light of the laser beam from the diffuse surface. Accordingly, the triangulation unit(s) 108 is configured to detect, from the reflective zinc-based coated surface, the diffuse light of the laser beam. In an embodiment, the triangulation unit 108 is used to determine the distance of the sheet 150 to the air knives 104. In another embodiment, the triangulation unit 108 is used to identify imperfections in the surface coating.

A laser triangulation unit is commonly used to determine a distance to a surface. It works by projecting a laser beam directly onto the surface to produce a laser dot, and using a camera (which may be referred to as a detector or sensor) to capture the angle of return of diffuse light of the laser dot relative to the detector of the laser triangulation unit. Upon hitting a diffuse surface, the laser beam is dispersed in all directions as diffuse light which gives the appearance of a laser dot to an observer. The distance between the camera and the laser emitter is known. The angle between the laser beam and a line between the emitter and detector is known. The angle between the emitted laser and returning diffuse light of the laser dot is known (which, in some cases, is based on the location of the laser dot in the camera's field of view). This distance and two angles are then used in a triangulation calculation to determine a value corresponding to the distance between the laser source and the diffuse surface. The value may be the actual distance traveled by the laser beam as collimated light, namely, the distance from the laser source to the target surface.

The conventional configuration of a laser triangulation unit cannot, however, determine the distance to a surface which is reflective. This is because a laser dot does not appear on a reflective surface. Rather than being dispersed as diffuse light, the laser beam is simply reflected by the reflective surface back to the laser emitter as collimated light. Accordingly, a laser triangulation unit in a conventional configuration cannot be used to detect the distances of an air knife to a molten zinc coating on a metal sheet. This is because, as portions of the metal sheet emerge from the bath, the zinc-based coating thereon may be molten making it reflective. In a conventional configuration, the laser beam from a triangulation unit does not produce a laser dot on the reflective molten coating. The laser beam merely reflects off of the reflective coating back to the laser emitter.

Figure 2A:
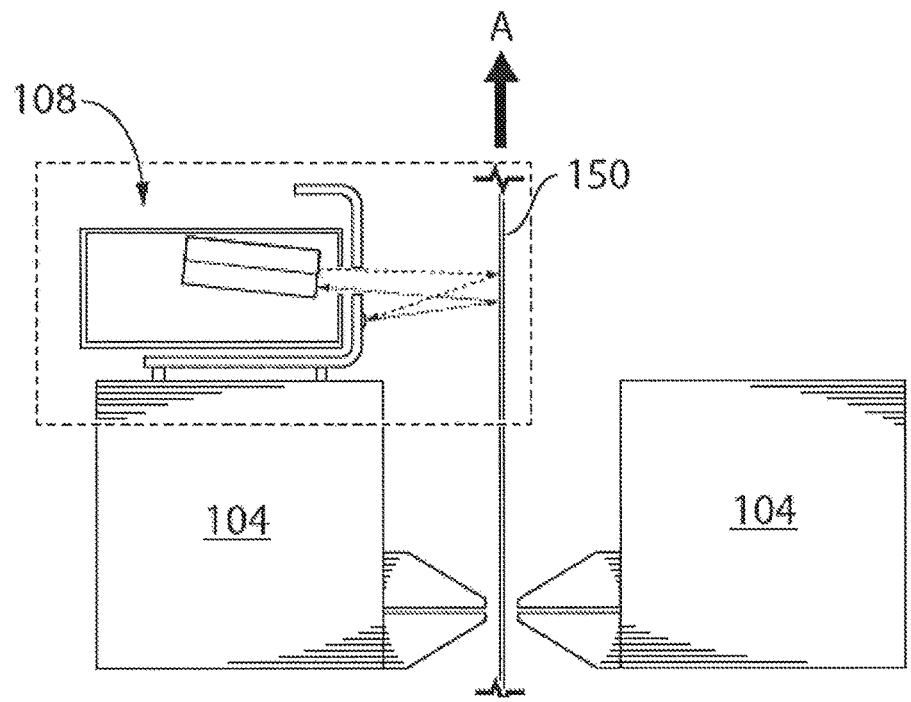
FIG. 2A shows a triangulation unit, and paths of light from its laser beam, of the system of FIG. 1 in greater detail in accordance with an embodiment of the present disclosure.
Figure 2B:
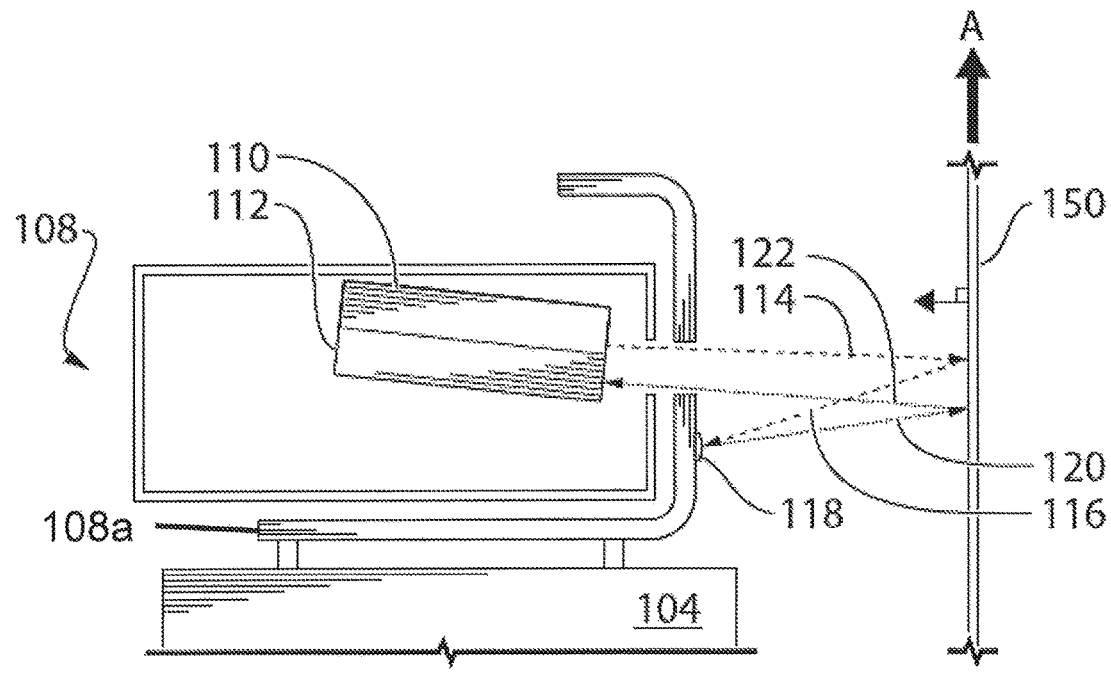
FIG. 2B shows the triangulation unit and sheet of FIG. 2A in greater detail, in accordance with an embodiment of the present disclosure.

FIGS. 2A and 2B shows a triangulation unit 108, and paths of light of its laser beam, of the system 100 of FIG. 1 in greater detail in accordance with an embodiment of the present disclosure. The triangulation unit 108 is configured such that the light source 110 emits a laser beam 114 with a direction of travel that is at an angle to the perpendicular of the plane of the sheet 150. The triangulation unit 108 may be so configured through its mounting. The angle of the laser beam 114 must be such to cause the beam 114 to reflect as a reflected beam 116 off of the reflective surface of the sheet 150, and project onto a target diffuse surface to produce a laser dot 118 the reflection of which in the reflective surface 150 is visible by the detector 112. If the beam is not at an angle to the perpendicular of the reflective surface 150, the beam will simply return to the laser source 110 as collimated light without any diffuse light from the beam reaching the laser detector 112. The diffuse surface may be a housing 108a, including the housing of the triangulation units 108.

When the reflected beam 116 hits the diffuse target surface, there is a dispersion of the reflected beam 116 as diffuse light 120. The diffuse light 120 gives the appearance of a laser dot 118 on the diffuse target surface to an observer (such as a person or a camera). The reflective surface 150 then reflects a portion of the diffuse light 120 of the laser dot 118 back to the detector 112 of the triangulation unit 108. In effect, the detector 112 receives, off the reflective surface 150, a reflection of the laser dot 118 on the diffuse target surface.

The triangulation unit 108 determines a value (takes a reading) based on the received diffuse light 120 of the laser dot 118. The value may correspond to the angle of travel of the diffuse light received by the detector 112. In a conventional configuration (namely, without a reflective surface), the reading of the laser triangulation unit 108 corresponds to the distance travelled by the laser beam 114 directly to the target diffuse surface as collimated light. The triangulation unit 108 is calibrated to determine this distance based on the return angle (angle of travel) of the diffuse light from the target diffuse surface. When the triangulation unit 108 is used in accordance with the embodiment shown in FIGS. 2A and 2B, however, the value the unit 108 determines corresponds to the distance traveled by the laser beam as collimated light inclusive of any reflections of that beam. Namely, the distance from the laser source to the reflective surface plus the distance from the reflective surface to the target diffuse surface. This distance corresponds with the return angle of the diffuse light of the reflected laser dot. In an embodiment, the value may be used by the computer 160 to calculate the actual distance of the reflective surface relative to a reference point such as the laser emitter 110.

The value from the triangulation unit 108 may be used to adjust the system to resolve issues with the metal sheet 150. In an embodiment, the distance between one or more air knives and the metal sheet 150 is adjusted. The adjustment may be to account for buckling and trembling of the sheet 150, for example, to maintain a select distance between each air knife 104 and the surface of the sheet 150. In an embodiment, the position of the air knives 104 is adjusted through movement of the frame 106, or a portion of the frame 106, with actuators upon which the air knives 104 are mounted. In another embodiment, the position of the sheet 150 is adjusted through movement of the rollers. In another embodiment, the tension of the rollers is adjusted.

Areas of the coating on a sheet 150 can have imperfections. The imperfections may be caused by, for example, contaminants or impurities in the bath 102 which find their way into the coating on the sheet 150. The imperfections may appear as bumps or inclusions in the coating. A bump is typically the inclusion below the surface of the coating. The appearance of the bump may be due to the meniscus of the coating metal around the inclusion.

In accordance with an embodiment of the present disclosure, the system 100 detects imperfections in a coating on the sheet 150. The computer 160 is programmed to help identify imperfections in the coating surface based on the readings from the triangulation unit 108 as the sheet 150 travels in a direction of its plane past the area or point being monitored by the triangulation unit 108. The computer 160 identifies the presence of imperfections in the coating by detecting variations in the triangulation unit readings. Those variations may be differences between readings. The variances in the readings, or differences between readings, which actually correspond to imperfections in a coating may be equal to or greater than a threshold amount. Imperfections on an area of the coating surface may appear as disturbances or noise in the corresponding readings of the triangulation unit 108 for that area. The disturbances may be very short, but high amplitude, readings, mostly caused by events other than genuine process changes. For example, where the readings are distance readings, a disturbance may appear as an increase of between 20 millimeters (mm) and 80 mm for a single scan (e.g. 10 milliseconds) in a reading which should be detecting a distance of about 250 mm. In other words, in an embodiment, a disturbance corresponding to between an 8% and a 32% increase in the distance readings may indicate the presence of an imperfection in the coating on the sheet. If there are many imperfections in a particular area, the disturbances can combine to give an average false distance. Such false distance readings can be detected and corrected, however, with sufficiently valid data over a longer period of time/greater sheet area so that the large number of imperfections can be identified.

The computer 160 may be programmed to amplify or distort the readings from the laser triangulation unit 108 to better detect differences between, or variations in, the readings corresponding to imperfections on the reflective coated surface. The computer may use an asymmetric mathematical filter to mask (i.e. filter) the effects of coating imperfections from the distance readings to obtain true distance measurements. A usable nominal position of the sheet/strip surface can be calculated by using this asymmetric filter. By comparing the filtered distance measurement against the unfiltered distance readings, the number of imperfections on the sheet/strip surface can be counted and reported. The number of imperfections observed (such as within a period of time or the length of coated sheet that has passed through the area being monitored by the triangulation unit) can be used as a surface coating quality index.

Figure 3:
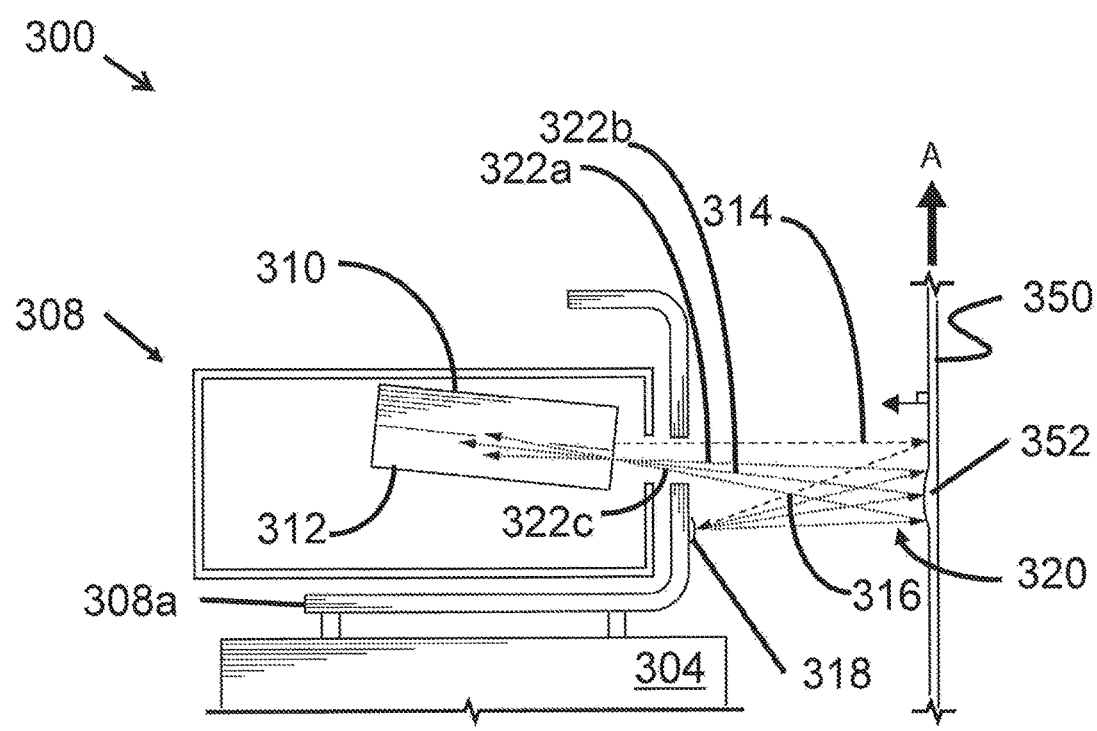
FIG. 3 shows, in accordance with an embodiment of the present disclosure, light paths of a laser beam from a system used on a reflective surface having an imperfection.

FIG. 3 shows, in accordance with an embodiment of the present disclosure, light paths of a laser beam from a system 300 used on a reflective surface 350 having an imperfection 352. The system 300 is similar to the system 100 of FIG. 1. A beam 314 from the laser emitter 310 reflects off reflect surface 350 so as to project 316 onto diffuse surface 308*a*.

The reflected beam 316 on the diffuse surface 308*a* produces a light dot 318 which provides a diffuse light 320 back towards the reflective surface 350. When reflecting off the reflective surface 350, the imperfection 352 in the coating changes what would have otherwise been the normal angles of return of the diffuse light 322*a*, 322*b*, 322*c* from the dot 318. (Laser dot 318 is shown as a raised bump in FIG. 3 to better illustrate the presence of the dot on the diffuse surface. The laser dot 318, however, does not in-fact produce a raised surface but rather conforms to the topology of the surface upon which it illuminates.) The detector detects the various angles of return of the diffuse light 322*a*, 322*b*, 322*c* as the imperfection moves past the area at which the laser beam is directed. The angle of one of the paths of returning diffuse light may be significantly greater than the angles of the other paths. Although three paths of the diffuse light 320, and the reflected diffuse light 322A 322*b*, 322*c* are shown for illustration purposes, it will be appreciated that the diffuse light of the laser beam comprises many paths traveling towards the lens/aperture of the detector 312.

A triangulation unit is typically configured to output a distance reading (also referred to herein as a measurement) of the longest distance possible based on the multiple diffuse light paths it detects. This is so that, for example, the unit does not under report the distance to a target diffuse surface due to detecting a shorter path of a portion of diffuse light caused by that portion prematurely reflecting off of air-born particulate between the detector and the target surface. In an embodiment, the triangulation unit 308 provides a reading for the stream of diffuse light, of the three light streams 322*a*, 322*b*, 322*c*, that has an angle of travel corresponding to what would be the longest distance in a conventional configuration of the unit 308. In this way, as the area of the surface with the imperfection 352 moves past the area in space being scanned by the laser beam of the triangulation unit 308, it results in a longer distance reading from the triangulation unit 108. In other words, when the portions of the surface 350 on either side of the imperfection 352 are scanned by the unit 308, the unit 308 reports normal distance readings, and when the portion of the surface having the imperfection 352 is scanned by the unit 308, the unit 308 reports a distance reading which is greater than the normal distance readings. The longer distance may appear in the readings for only a brief period of time.

Since the galvanization process of the system 100 is continuous, the laser triangulation unit 108 may output a series of laser beams as a light signal. The light signal may comprise pulses of laser beams, each pulse lasting for 35-45 nanoseconds. Each pulse may result in a single reading from the triangulation unit 108. The laser beam may be output for a period of time as the sheet is moved in the direction of its plane shown by arrow A in FIG. 3. The diffuse light of the laser beam hits the same area in space, but the portion of the surface of the sheet at that area changes over time as the sheet moves in the direction of its plane. The detector may take continuous or discreet readings of the continuous stream of diffuse light reflecting off the different portions of the coated sheet surface. A difference greater than a threshold amount between two consecutive readings may indicate an imperfection on the portion of the surface corresponding to one of those readings.

Figure 4:
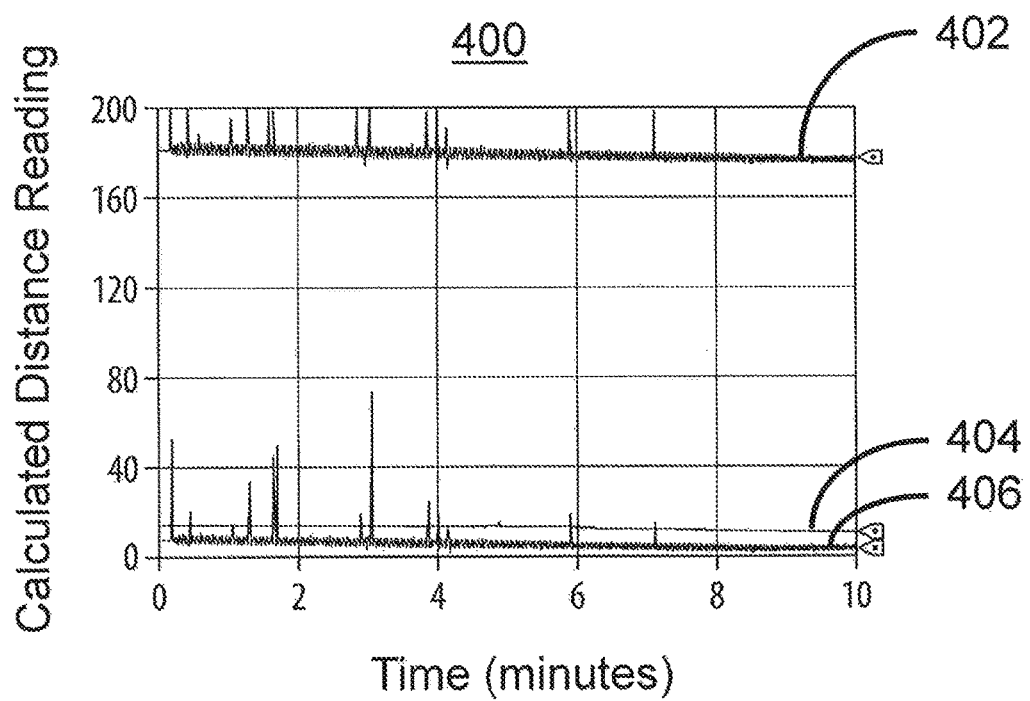
FIGS. 4 and 5 show representative graphs of data, as may be generated in the system of FIG. 1 when processing a reflective surface with minimal imperfections, and processing a reflective surface with many imperfections, respectively.
Figure 5:
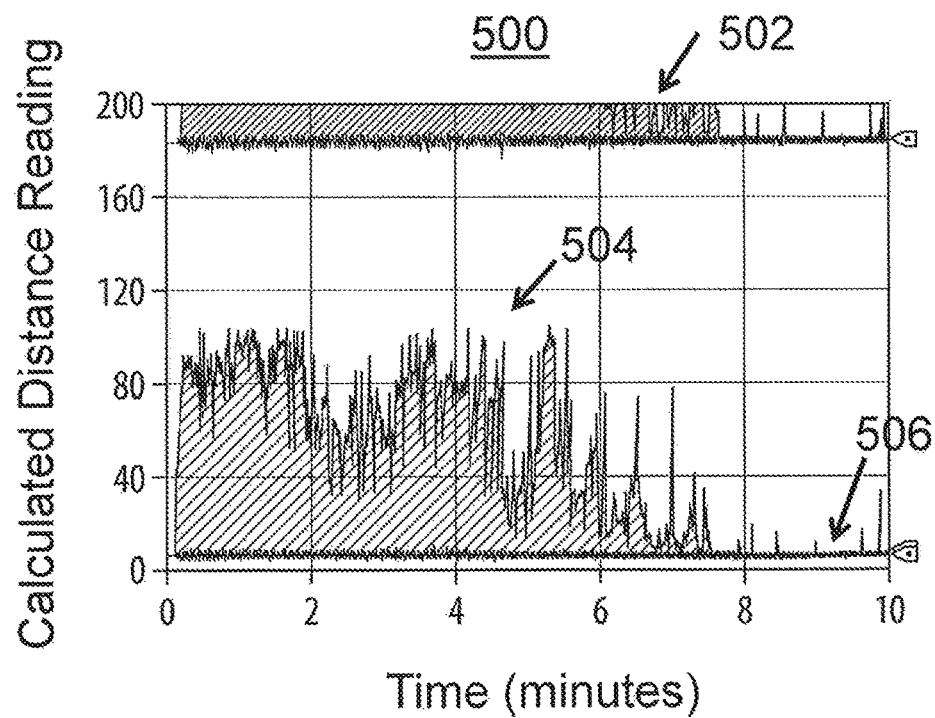

FIGS. 4 and 5 show representative graphs 400, 500 of plots 402, 404, 406 of data from a reflective surface with minimal imperfections, and plots of data 502, 504, 506 from a reflective surface with imperfections, respectively, as may be generated in the system 100 of FIG. 1. The X-axis of each graph 400, 500 shows a 10-minute time period in 2-minute increments. The Y-axis of each graph 400, 500 show values corresponding to calculated distance readings from the laser triangulation unit. Graph 400 corresponds to a metal sheet 150 with minimal imperfections in the metal coating surface scanned by the system 100. Graph 500 corresponds to a metal sheet 150 with many imperfections in the metal coating surface scanned by the system 100.

Plots 402, 502 are of the distance readings received by the computer 160 from the triangulation unit 108. Plots 404, 504 show amplified normalized distance readings from the triangulation unit 108. Normalization may be performed by subtracting a value proportional to the actual distance of the triangulation unit 108 from the sheet 150. Plot 406, 506 correspond to the distance readings from the triangulation unit 108 after those readings have been filtered by the computer 160 to reduce noise.

Plot 404 shows normal distance readings, a low level of noise in the readings signal, and distance readings which are generally stable. By contrast, plot 504 shows the distance readings having a higher overall average and noise just after minute 0 and up until just before minute 6. Between minute 6 and minute 8, the noise dissipates and the overall distance reading average is lower. And from minute 8 onward, the distance average and noise is minimal. The higher distance reading averages and noise in graph 500 are the result of imperfections in the coating on the sheet 150 as those imperfections passed by the area scanned by the laser beam of the triangulation unit 108. The reading noise pattern observed in plot 504 may be the result of adding a zinc ingot into the bath 102 to replenish the zinc-based material.

In an embodiment, the computer 160 is programmed to determine the quality of a coating for a portion of a sheet based on the number of imperfections detected in a period of time or length of sheet. The period of time may be one second. The length of sheet may be between 1 and 10 meters. The number of readings from the laser triangulation unit in one second may be between 1 and 90.

In an embodiment, the computer 160 outputs a report of coating imperfections. The report may be updated on a real-time, or nearly real-time basis. In an embodiment, the computer 160 may be configured to stop the coating process in response to reaching a threshold number of imperfections.

The system 100 helps detect imperfections in the surface coating at an early stage in the galvanization process. Namely, as soon as the sheet emerges from the bath of the galvanization material and the coating is still molten. Early detection of imperfections may allow for a number of actions to be taken which may not otherwise be possible if the imperfections are detected at a later stage (i.e. downstream in the process). Early detection may allow for quicker remediation of the cause of the imperfections thereby limiting the amount of product (e.g. area of the sheet) affected by imperfections. Early detection may make it easier to determine the actual cause of the imperfections. The galvanization process may then be modified to help reduce or eliminate the cause of the imperfections. For example, if the cause of certain coating surface imperfections is the placement of a zinc-ingot in the bath, one or more of: the ingot may be pre-washed before placement; the line may be slowed or stopped for a period of time until the impurities from the ingot are removed or pushed to the sides of the bath by the air from the air knives; the placement of the ingot in the bath may be timed with the changing between sheets so that only the start and/or end of the sheets, and not a middle portion of the sheet, are materially affected by imperfections; ingots may be only added to the bath when products with lower standard surface requirements are being immersed in the bath. In an embodiment, the computer 160 may be configured to take a certain action to help address/avoid imperfections (including the occurrence of further imperfections) in the coating in response to the detection of an imperfection according to the an embodiment of the present disclosure. For example, the computer 160 may be configured to control the actuators to adjust the distance of the air knives relative to the sheet. Detection of the imperfections while the coating is still molten may allow certain actions to be taken to reduce or eliminate the imperfections (including occurrences of further imperfections). Early detection of the imperfection may allow for early identification and potentially removal, in the galvanization process line, of that portion of the sheet affected by imperfections.

The system 100 can also be simultaneously used to determine the distance of air knive(s) to the sheet. This may help save cost by reducing the amount of equipment required/using the same equipment for multiple purposes, and simplifying the design and implementation of a galvanization system.

Figure 6:
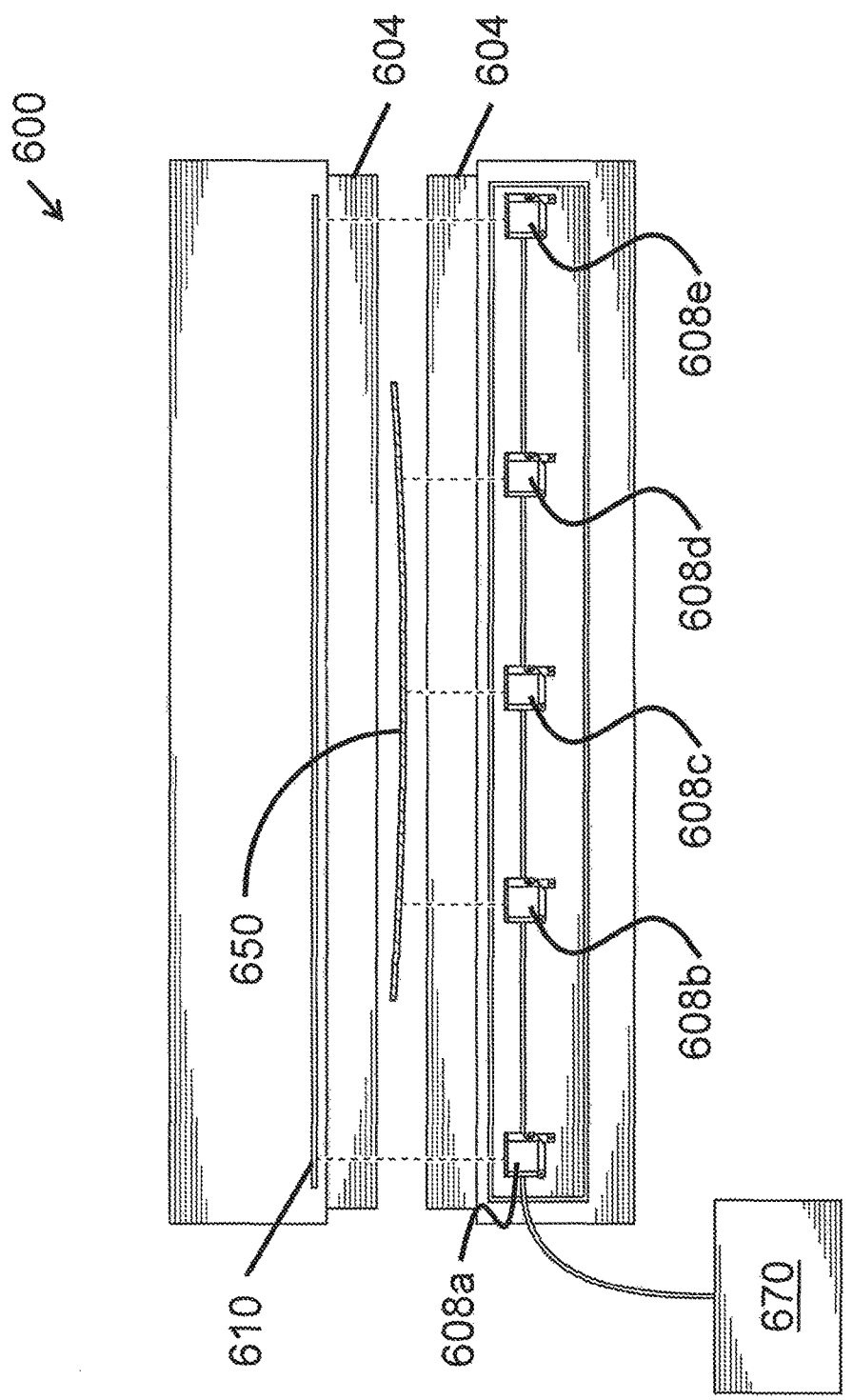
FIG. 6 shows a top view of system 600 in accordance with an embodiment of the present disclosure.

FIG. 6 shows a top view of a system 600 in accordance with an embodiment of the present disclosure. The system 600 is similar to the system 100 of FIG. 1. The system 600 comprises a plurality of triangulation units 608a-e mounted along the length of an air knife 604 as a planar array. This configuration permits the monitoring of the distance of the sheet 650 to the air knife 604 at various points along the sheet 650 to help measure, for example, the bow of the sheet 650. Bowing of the sheet 650 can result in some portions of the sheet 650 being closer to the air knife 604 than others, potentially resulting in an uneven coating being applied. Bowing information can be used to correct such bowing through, for example, changing tensions of rollers guiding the sheet through the air knifes.

The two end laser triangulation units 608a, 608e (also referred to as reference laser triangulation units) are mounted beyond the width of the sheet 650. In this way, the triangulation units 608a, 608e detect the distance from the air knife 604 to points (such as a panel 610) on the opposite air knife 604 as a reference measurement.

The coating on the sheet 650 can be presented to triangulation units in either a molten or solidified form. A molten coating is a reflective surface, a solid coating is diffuse surface. A coating that is transitioning between a molten state and a solid state may have varying reflectivity. The readings from the laser triangulation unit for a molten zinc-coated surface are very different than the readings for a solid/hardened zinc-coated surface. For the solid coating, the readings correspond to the actual distance to the sheet 650. For a molten coating, the readings correspond to the angle of travel of diffuse light, of the laser beam, reflecting off of the reflective surface. This angle of travel may not correspond to any actual distance. The actual distance to a reflective surface may be proportional to half the distance reading from the laser triangulation unit due to the additional distance traveled by the laser beam as a result of its reflection. The distance reading of a triangulation unit 608b-d can be compared to a reference distance to determine whether the distance readings are of a solidified coating or a molten coating. The reference distance may be a reading from reference triangulation units 608a and/or 608e which are outside the width of the sheet/strip 650. A reference distance may be obtained through manual measurement at the time of setting up the system 600. Alternatively, the reference distance may be based on motor position feedback data for the air knife 604. If a distance reading is greater than the motor position feedback data by a threshold amount, then the laser beam for the distance reading must have been reflected. Alternatively, the reference distance may be a value greater than the maximum distance an air knife 604 could be from the sheet 650. Such maximum distance may be based on a physical limitation of how far the air knife 604 could be from the sheet 650.

A reference distance can also allow determination of the distance from both air knifes to their respective sheet 650 surfaces without the need for having distance detection devices on both sides of the sheet 650. This can help reduce cost and complexity. In an embodiment, the computer 670 compares the readings from the reference triangulation units 608*a,e* to the readings from the other triangulation units 608*b-d* to determine the distance of the sheet 650 from both air knifes 604 at various points.

Figure 7:
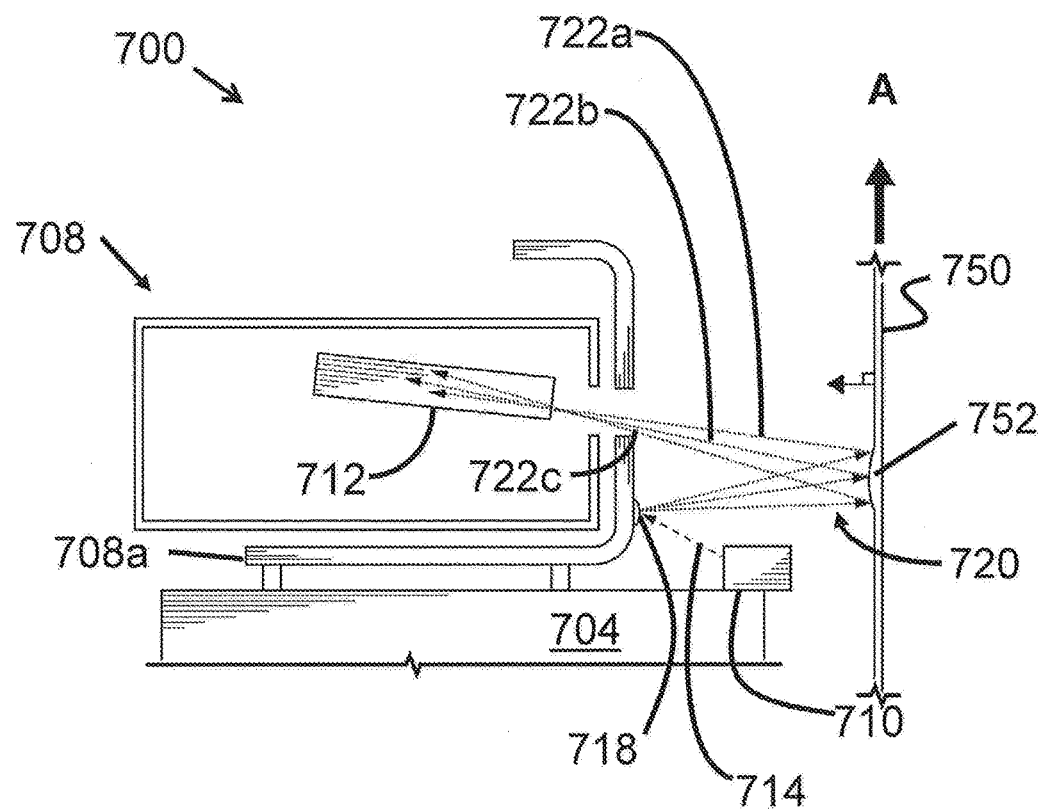
FIG. 7 shows a system, similar to the system of FIG. 3, but comprising a laser emitter that is separate from the laser detector, in accordance with another embodiment of the present disclosure.

FIG. 7 shows a system 700 in accordance with another embodiment of the present disclosure. The system 700 is similar to the system 300 of FIG. 3, the difference being that it comprises a laser emitter 710 and a detector 712 which are separate from one another, and not within a single unit 708. In this embodiment, the laser emitter 710 emits a laser beam 714 directly at the diffuse surface 708*a* to produce a laser dot 718. The diffuse light 720 of the laser dot 718 (comprises multiple paths) reflects off the imperfection 752 to produce multiple paths of diffuse light 722*a*, 722*b*, 722*c* that intersect at the lens/aperture of the detector 712. The different angles of the diffuse light 722*a,b,c* are detected by the detector 712 to produce a reading. In this case, the reading of the detector 712 has little to do with the actual distance of the reflective surface 750 from the detector 712.

I claim:

1. A system for detecting imperfections in a reflective surface, comprising:
    a laser triangulation unit configured to emit a laser beam and detect, from the reflective surface, diffuse light of the laser beam; and
    a computer configured to
        receive readings from the laser triangulation unit, the readings corresponding to angles of travel of the diffuse light, and
        identify imperfections in the reflective surface based on variances between the readings for different portions of the reflective surface.

2. The system of claim 1 for use in a metal sheet galvanization process, wherein the reflective surface is a molten coating on a metal sheet.

3. The system of claim 2, further comprising an air knife for directing air on the molten coating on the sheet, and wherein the computer is further configured to determine the distance between the air knife and the reflective surfaces based on the readings.

4. The system of claim 3, further comprising an actuator for controlling the distance of the air knife to the sheet, the computer configured to cause the actuator to adjust the distance of the air knife to the sheet in response to the readings.

5. The system of claim 1, wherein the computer is configured to identify an imperfection in the reflective surface based on a first reading being greater than a second reading by a threshold amount.

6. The system of claim 1, wherein the computer is configured to identify an imperfection in the reflective surface based on a disturbance in the readings.

7. The system of claim 6, wherein the computer is configured to determine the number of the disturbances in the readings within a period of time.

8. The system of claim 1, wherein the triangulation unit is configured to provide a reading corresponding to the portion of the diffuse light having the longest distance of travel.

9. The system of claim 1, wherein the laser triangulation unit is configured to project the laser beam off of the reflective surface onto a diffuse surface to produce the diffuse light.

10. The system of claim 9, wherein the laser triangulation unit its configured to emit the laser beam at the reflective surface at an angle to the perpendicular of the reflective surface.

11. The system of claim 1, wherein the laser triangulation unit comprises a housing with a diffuse surface, and wherein the laser triangulation unit is configured to project the laser beam on the housing to produce the diffuse light.

12. A system for identifying imperfections in a reflective coating on a metal sheet in a galvanization process, comprising;
    a laser emitter configured to emit a laser beam at the reflective coated surface of the metal sheet, at an angle to the perpendicular of the surface, to project a laser dot on a diffuse surface;
    a detector configured to detect, from the reflective coated surface, the angles of travel of diffuse light of the laser dot from the diffuse surface; and
    a processor configured to identify imperfections in the reflective coating based on variances in the readings of the detector for different portions of the reflective surface.

13. A method for detecting imperfections in a reflective surface, comprising:
    detecting, off the reflective surface, diffuse light of a laser beam;
    determining values corresponding to the angles of travel of the detected diffuse light; and
    identifying imperfections in the reflective surface based on variances in the values.

14. The method of claim 13, for use in a metal sheet galvanization process, wherein the reflective surface is a molten coating on the metal sheet.

15. The method of claim 13, wherein determining the values comprises determining the distances travelled by the laser beam as collimated light.

16. The method of claim 15, where the distances are determined based on triangulation.

17. The method of claim 13, wherein imperfections in the reflective surface are identified based on a first value being greater than a second value by a threshold amount.

18. The method of claim 13, wherein imperfections in the reflective surface are identified based on disturbances in the values.

19. The method of claim 18, further comprising determining the number of disturbances occurring in a period of time.

20. The method of claim 13, further comprising emitting the laser beam.

21. The method of claim 20, wherein the laser beam is projected off the reflective surface onto a diffuse surface to produce the diffuse light.

22. The method of claim 21, wherein the laser beam is emitted et the reflective surface at an angle to the perpendicular of the reflective surface.

23. The method of claim 13, wherein the reflective surface is moved in the direction of its plane relative to the path of the diffuse light.

* * * * *